| United States Patent [19] | [11] Patent Number: 4,943,647 |
| Band et al. | [45] Date of Patent: Jul. 24, 1990 |

[54] PREPARATION OF HEXAALKYLDISILTHIANE

[75] Inventors: Elliot I. Band, North Tarrytown, N.Y.; Suzanne T. Eberhart, New Haven, Conn.

[73] Assignee: Akzo America Inc., New York, N.Y.

[21] Appl. No.: 330,575

[22] Filed: Mar. 30, 1989

[51] Int. Cl.$^5$ ................................................ C07F 7/08
[52] U.S. Cl. .................................................... 556/426
[58] Field of Search ......................................... 556/426

[56] References Cited

U.S. PATENT DOCUMENTS 3,344,161  9/1967  Moedritzer et al. ................. 556/426

OTHER PUBLICATIONS

Moehs et al., "J. Org., Nucl. Chem.", 43, No. 2, 1981, pp. 235–237.
Olah et al., "J. Org. Chem.", 44, No. 24, pp. 4272–4275 (1979).
Chanpetier et al., "Compt. Rend.", 234, pp. 1985–1986 (1952).
Detty et al., "J. Org. Chem.", 47, 1982, pp. 1354–1356.

*Primary Examiner*—Paul F. Shaver
*Attorney, Agent, or Firm*—Richard P. Fennelly; Louis A. Morris

[57] ABSTRACT

Hexaalkyldisilthiane compounds (e.g., hexamethyldisilthiane) are synthesized by reaction of lithium disulfide and a halotrialkylsilane (e.g., chlorotrimethylsilane) in a non-oxygenated solvent (e.g., acetonitrile).

7 Claims, No Drawings

PREPARATION OF HEXAALKYLDISILTHIANE

BACKGROUND OF THE INVENTION

1. Field of the Invention

The present invention relates to a novel process for the preparation of hexaalkyldisilthiane.

Description of the Prior Art

Hexaalkyldisilthiane (e.g., hexamethyldisilthiane) are currently of interest in regard to use as solid electrolytes for rechargeable batteries. Improved processes for the manufacture of such compounds is an area of active interest.

G. Champetier et al. in Compt. rend. 234, 1985-1986 (1952) indicated that only small quantities of hexamethyldisilthiane were produced when trimethylchlorosilane and lithium sulfide were reacted with the main product (at 48% yield) being trimethylthiosilane.

More recently, G. A. Olah et al., in J. Org. Chem., Vol. 44, No. 24, pp. 4272–4275 (1979), in footnote 13, indicated that "hexamethyldisilathiane" could be prepared from sodium sulfide and chlorotrimethylsilane at high temperatures in pressure reactors but also stated that there was almost no reaction between lithium sulfide and chlorotrimethylsilane at room temperature and atmospheric pressure.

M. R. Detty et al. in J. Org. Chem. 1982, 47, 1354-1356 reiterated the above statement about the substantial nonreactivity of lithium sulfide and chlorotrimethylsilane and indicated that commercially available dilithium sulfide and chlorotrimethylsilane, when refluxed for seventy-two hours in tetrahydrofuran, gave only a 45% yield of hexamethyldisilthiane, also called "bis(trimethylsilyl)sulfide.

SUMMARY OF THE INVENTION

The present invention relates to the production of a predominant amount of hexaalkyldisilthiane in the product of the reaction of lithium sulfide and halotrialkylsilane in a non-oxygenated solvent.

DETAILED DESCRIPTION OF THE INVENTION

The hexaalkyldisilthiane compounds produced by the instant process have the formula

$R_3SiSSiR_3$ where R is a lower alkyl group, such as methyl, ethyl, propyl, isopropyl or the like having from one to eight carbon atoms. The lithium sulfide reactant is dilithium sulfide and is commercially available. The halotrialkylsilane reactant is preferably a chlorotrialkylsilane with chlorotrimethylsilane being most preferred.

The reaction between the chosen silane reactant and dilithium sulfide can take place using molar ratios of the former to the latter of from about 2:1 to about 10:1 at temperatures ranging from about 20° C. to about 100° C. The solvent medium for the reaction is a non-oxygenated solvent including the aliphatic and aromatic hydrocarbons and their derivatives (e.g., the halogenated and cyano derivatives). Acetonitrile, a highly polar solvent having a high dielectric constant is a preferred example.

The synthetic conditions used are relatively mild and the yield of product is good.

The following Example further illustrates the invention.

EXAMPLE 1

This Example describes the preparation of hexamethyldisilthiane.

To a dry, nitrogen purged, 100 ml flask containing a stir bar 2.30 grams, 50 mmol, of commercial $Li_2S$ from Aldrich was added followed by about 15 grams of dry acetonitrile. Then 10.9 grams, 100 mmol, of chlorotrimethylsilane was added by syringe. The vessel was stirred at room temperature for about sixty-five hours and then refluxed five hours. The reaction was monitored by $^1H$ nmr spectroscopy and the nmr spectra showed the starting silane slowly disappeared and was replaced quantitatively by a resonance at sigma= $-1.58$ ppm vs. acetonitrile consistent with a quantitative conversion to $((CH_3)_3Si)_2$ S. The product solution was isolated by filtration and contained under 0.01 wt % residual Li in solution (over 99 mole % of lithium remaining behind as a solid).

The foregoing Example is presented for illustrative purposes and should not therefore be construed in a limiting sense. The scope of protection which is sought is set forth in the claims which follow.

We claim:

1. A process for preparing a product which is predominantly hexaalkyldisilthiane which comprises the reaction of dilithium sulfide and halotrialkylsilane in a non-oxygenated solvent.

2. A process as claimed in claim 1 wherein the halotrialkyl silane is chlorotrimethylsilane.

3. A process as claimed in claim 1 wherein the reaction is conducted at from about 20° C. to about 100° C.

4. A process as claimed in claim 2 wherein the reaction is conducted at from about 20° C. to about 100° C.

5. A process as claimed in claim 1 wherein the solvent is acetonitrile.

6. A process as claimed in claim 2 wherein the solvent is acetonitrile.

7. A process as claimed in claim 3 wherein the solvent is acetonitrile.

* * * * *